United States Patent [19]

Takemura et al.

[11] 4,372,323
[45] Feb. 8, 1983

[54] ULTRASONIC DIAGNOSING APPARATUS

[75] Inventors: Yasuhiko Takemura, Nishinasuno; Takahisa Okazaki, Otawara; Akira Imai, Urawa, all of Japan

[73] Assignee: Tokyo Shibaura Denki Kabushiki Kaisha, Japan

[21] Appl. No.: 170,178

[22] Filed: Jul. 18, 1980

[30] Foreign Application Priority Data

Jul. 20, 1979 [JP] Japan ............... 54-91675

[51] Int. Cl.³ .................... A61B 10/00
[52] U.S. Cl. .................. 128/660; 73/625
[58] Field of Search ............ 128/660-663; 73/626, 625

[56] References Cited

U.S. PATENT DOCUMENTS

| | | | |
|---|---|---|---|
| 3,789,833 | 2/1974 | Bom | 128/2 |
| 4,070,905 | 1/1978 | Kossoff | 128/660 X |
| 4,078,435 | 3/1978 | Kossoff et al. | 128/660 X |
| 4,135,140 | 1/1979 | Buchner | 73/626 |
| 4,159,462 | 6/1979 | Rocha et al. | 73/626 X |
| 4,161,121 | 7/1979 | Zitelli et al. | 128/660 |
| 4,234,940 | 11/1980 | Iinuma | 73/626 X |
| 4,274,422 | 6/1981 | Anderson et al. | 128/661 |

OTHER PUBLICATIONS

"Electronic Sector Scanning in the Diagnosis of Cerebrovascular Disease and Space-Occupying Processes", Hans J. Freund et al., Neurology, vol. 23, No. 11 (11/73), pp. 1147-1159.

*Primary Examiner*—Kyle L. Howell
*Assistant Examiner*—Francis J. Jaworski
*Attorney, Agent, or Firm*—Finnegan, Henderson, Farabow, Garrett & Dunner

[57] ABSTRACT

An electronic linear scan mode and an electronic sector scan mode are selectively used individually or in combination under the control of a mode selection means provided for determining a scan mode for an ultrasonic probe consisting of a plurality of ultrasonic transducers the ultrasonic wave transmission and reception timing of which is controlled by a scanning control means in accordance with the determined scan mode.

6 Claims, 11 Drawing Figures

ULTRASONIC DIAGNOSING APPARATUS

This invention relates to an ultrasonic diagnosing apparatus of a commonly termed electronic scan system, in which ultrasonic pulse beams are projected from a plurality of ultrasonic transducers through electronic scanning to obtain a tomogram of an object under examination from pulse echoes resulting from these pulse beams.

To date, an ultrasonic diagnosing apparatus of this kind enables observation by tomography of the moving heart and other organs of a human body so that it is a very powerful tool for the diagnosis of diseases and troubles in such portions of the body. In electronic scan systems, there are linear and sector scan techniques which are selectively used depending upon the purpose of the diagnosis.

In the electronic linear scan system, basically a probe consisting of a number of (namely n) ultrasonic transducers arranged in a row is used, and these transducers are successively driven from the first to the n-th transducer by electronic scanning to produce successive or sequential ultrasonic pulse beams and receive pulse echoes resulting from their own projected beams so as to obtain a real time display of a tomogram within a scanning area parallel to the probe on a CRT display set. In this system, if it is intended to increase the image density by reducing the scanning line interval, it is necessary to increase the number of transducers per unit length of the row by reducing the width of the transducer. In this case, the directivity of the ultrasonic beam is diminished, so that it is likely that echoes coming from points other than the centerline of the projected beam are received and that a proper image cannot be obtained. Accordingly, it has been in general practice to successively drive a group of m (for instance eight) transducers out of n (for instance sixty-four) transducers at a time for producing m simultaneous beams and sum up the resultant m echoes so as to regard the sum of the echoes to be an echo coming from a point in a scanning line normal to and passing through the center of the group of the m simultaneously driven transducers. In such a manner, it is possible to make the directivity of the ultrasonic beam sharper and increase the resolution, and in effect a tomogram produced with $(n-m+1)$ parallel scanning lines is displayed on the CRT.

In an electronic sector scan system, on the other hand, a smaller number of transducers than that in the case of the electronic linear scan system, for instance thirty-two transducers, are driven one after another at a predetermined delay time so that the ultrasonic beams produced from them overlap and the resultant wave front (i.e., plane of the same phase) is directed in a predetermined direction. The echoes resulting from the individual projected beams are received by the same transducers as for the individual projected beams under the same delay condition as at the time of the projection and are summed up together to regard the resultant echoes to be one coming from a point on the center line of the wave front propagating in the predetermined direction. The delay time is progressively varied for the individual transducers for sector scanning with ultrasonic beams. The individual ultrasonic beams are generated with respective sector angles so as to effect sector scanning over a predetermined angle range (for instance 78 degrees), and a tomogram within this scanning range is displayed on the CRT display set.

In the afore-mentioned electronic linear scan system, there is one, in which, when m transducers are driven at a time, the individual transducers are driven twice with a slight phase difference, (i.e., delay time) provided to effect sector scanning over a small angle (for instance 0.46 degree) (which is called small angle sector). In this case, two beams (of $+0.46$ degree and $-0.46$ degree) are obtained from the same set of transducers, and in effect the number of the scanning lines is doubled compared to the case of the ordinary electronic linear scan system.

Further, since in either the electronic linear or sector scan system by driving a plurality of transducers at a time the width of the beam itself is increased to deteriorate the lateral resolution, it has been known in practice to provide what is called electronic focusing, which makes use of the beam deflecting effect provided by delaying the drive timing of a plurality of transducers one after another, in either of the two electronic scan systems. More particularly, it has been known in practice to set the delay time at the time of the afore-mentioned sector scanning such that the wave front of the ultrasonic wave is a concave surface so that the ultrasonic beam from the group of the simultaneously driven transducers is focused at the probed portion of the body.

The electronic linear scan system is suited for diagnosing moving organs in the abdomen, while the electronic sector scan system is suited for diagnosing the heart for it can project ultrasonic waves between adjacent ribs because it has a smaller number of transducers while it also generates a wave front which spreads in the inside of the body. Thus, these electronic scan systems are selectively used depending upon the probed portion of the body.

While in the ultrasonic diagnosing apparatus using the electronic scan system the two different types of electronic scan systems, i.e., electronic linear and sector scan systems, have been adopted, there has hitherto been no ultrasonic diagnosing apparatus which can be used either in the linear scan mode or in the sector scan mode, that is, it has been necessary to have two separate sets of diagnostic apparatus in order to be able to selectively use these two different scan systems or modes depending upon the probed portion of the body.

This invention has been intended in the light of the above aspect, and its first object of the invention is to provide an ultrasonic diagnosing apparatus which permits two different electronic scan modes, namely linear and sector scan modes, to be selectively obtained.

A second object of the invention is to provide an ultrasonic diagnosing apparatus, which enables two tomograms, based upon the same scan mode, to be displayed on a time division basis.

Another object of the invention is to provide an ultrasonic diagnosing apparatus which enables two tomograms, based upon different scan modes, to be displayed on a time division basis.

A further object of the invention is to permit the above objects of the invention to be selectively achieved with a single ultrasonic diagnosing apparatus.

This invention can be more fully understood from the following detailed description when taken in conjunction with the accompanying drawings, in which.

In one embodiment of the invention to be described hereinafter, five different electronic scan modes can be selectively used. The five electronic scan modes are as follows:

(1) Electronic linear scan mode (hereinafter referred to as L mode)

This mode is already in practical use as mentioned earlier, that is, in this mode a tomogram is displayed on a CRT, the small angle sector and electronic focusing being provided in the embodiment. In the embodiment, an ultrasonic probe consisting of seventy one transducers is used, and these transducers are successively driven eight at a time to obtain sixty-four scanning lines for a first field with a small angle sector of $+\alpha°$ provided therefor and another sixty-four scanning lines for a second field with a small angle sector of $-\alpha°$ provided therefor so as to obtain a tomogram through interlaced scanning with one hundred and twenty-eight scanning lines per frame.

(2) Electronic sector scan mode (hereinafter referred to as S mode)

This mode is also already in practical use as mentioned earlier, a tomogram is displayed on a CRT, the electronic focusing being provided in this embodiment. In this embodiment, an ultrasonic probe consisting of thirty-two transducers is used to obtain sixty-four scanning lines with respective odd number deflection angles $\theta_1, \theta_3, \theta_5, \ldots, \theta_{127}$ for a first field and another sixty-four scanning lines with respective even number deflection angles $\theta_2, \theta_4, \theta_6, \ldots, \theta_{128}$ for a second field, a spread angle $\theta$ being provided, so as to obtain a tomogram through interlaced scanning with one hundred and twenty-eight scanning lines for one frame (i.e., two fields).

(3) Electronic linear/linear scan mode (hereinafter referred to as L/L mode)

In this mode, two probes for the L mode are used and alternately scanned each for one field period on a time division basis, and in effect two L mode tomograms of different portions or taken in different directions are simultaneously displayed on a CRT display unit (in the embodiment on respective CRTs).

(4) Electronic sector-sector scan mode (hereinafter referred to as S/S mode)

In this mode, two probes for the S mode are used and alternately scanned each for one field period on a time division basis, and in effect two S mode tomograms of different portions or taken in different directions are simultaneously displayed on a CRT display unit (in the embodiment on respective CRTs).

(5) Electronic linear/sector scan mode (hereinafter referred to as L/S mode)

In this mode, a probe for the L mode and a probe for the S mode are used and alternately scanned each for one field period on a time division basis, and in effect two tomograms, one in the L mode and the other in the S mode, of different portions or taken in different directions are simultaneously displayed on a CRT display unit (in the embodiment on respective CRTs).

Figure 1:
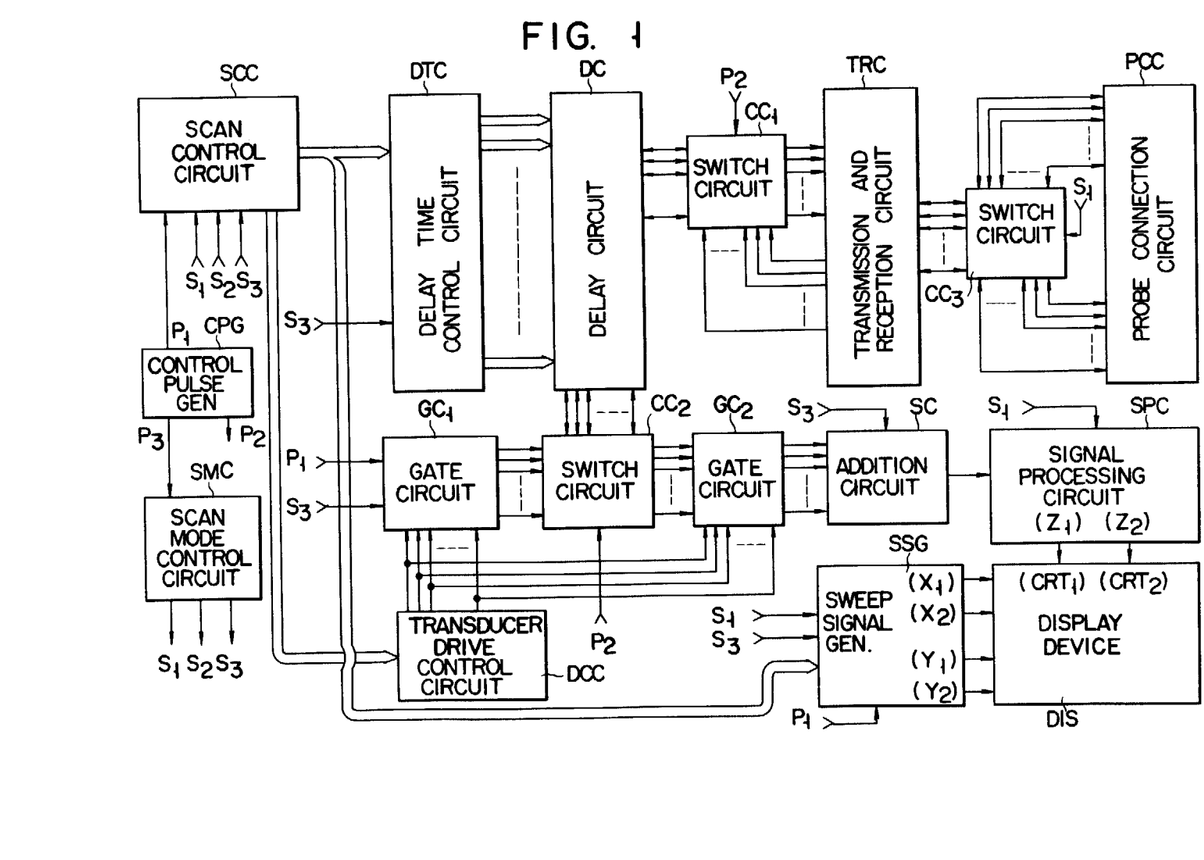
FIG. 1 is a block diagram outlining the main construction of the ultrasonic diagnosing apparatus according to the invention.

FIG. 1 shows the configuration of the main portion of one embodiment of the apparatus according to the invention. A scan mode selection circuit SMC includes a means for selecting the afore-mentioned five scan modes and a means for producing scan mode control signals $S_1$ to $S_3$. A control pulse generator circuit CPG produces a reference control pulse signal $P_1$ for determining the scan rate, a control pulse signal $P_2$ for determining the period, during which the system is held in an ultrasonic beam projection state, and a control pulse signal $P_3$ corresponding to the field period, the control pulse signals $P_2$ and $P_3$ being produced on the basis of the reference control signal $P_1$. A scanning control circuit SCC produces a scanning control signal (a digital signal) corresponding to the selected scan mode on the basis of the scan mode control signals $S_1$ to $S_3$ and reference control pulse signal $P_1$. A transducer drive control circuit DCC produces a drive control signal for successively driving eight L mode probe transducers on the basis of the scan mode control signals. A delay time control circuit DTC controls the delay time for the sector scanning and electronic focusing in each scan mode on the basis of the scanning control signal and the scan mode control signal $S_3$.

A delay circuit DC adequately delays the drive trigger signals or echo signals for respective transducers according to control signals from the delay time control circuit DTC. A transmission/reception circuit TRC produces a drive signal for each transducer from each of the adequately delayed drive trigger signals and also receiving and adequately pre-amplifying the echo signals. A first switching circuit $CC_1$ is controlled by the control pulse $P_2$ for switching between a first connection state in which drive trigger signals are supplied from the delay circuit DC to the transmission/reception circuit TRC and a second connection state in which echo signals are supplied from the transmission/reception circuit TRC to the delay circuit DC. A first gate circuit $GC_1$ is controlled by the scan mode control signal $S_3$ to assume a first state in which it passes the reference control pulse signal $P_1$ that constitutes the drive trigger signals to the succeeding stage under the control of the drive control signal from the transducer drive control circuit DCC and a second gate control state it passes the drive trigger signals without being controlled by the drive control signal. In other words, at the time of the L mode it effects gate control on the drive trigger signals such as to drive only eight among seventy-one L mode probe transducers that are determined by the drive control signal, while at the time of the S mode it effects gate control on the drive trigger signals such as to drive all the thirty-two S mode probe transducers. A second gate circuit $GC_2$ passes only echo signals from eight transducers to be received, as determined by the drive control signal, to the succeeding stage at the time of the L mode. A summing circuit SC sums and amplifies the echo signals from the preceding stage in the L and S modes separately and supplies the sum of echo signals in either mode to the succeeding stage according to the scan mode control signals $S_1$ and $S_3$.

A signal processing circuit SPC effects logarithmic amplification of the sum of echo signals and also gain control and other controls and supplies a video signal as brightness signal to a display unit DIS for detection and display on a CRT monitor. A sweep signal generator circuit SSG produces X and Y sweep signals according to the control signal from the scanning control circuit and reference control pulse signal $P_1$, the X and Y sweep signals being independently supplied to the display unit DIS for the respective scan modes according to the scan mode control signals $S_1$ to $S_3$. A probe connection circuit PCC functions to connect a first L or S mode probe to a first connection section at the time of the L or S mode, connect first and second L or S mode probes to respective first and second connection sections at the time of the L/L or S/S mode and to connect the first L and S mode probes to the respective first and second connection sections at the time of the L/S mode. A third switching circuit $CC_3$ is similar to the first and second switching circuits $CC_1$ and $CC_2$. It is controlled by the scan mode control signal $S_1$ to assume a first connection state connecting the transmission/reception circuit TRC and the probe connected to the first connection section of the probe connection circuit and a second connection state connecting the transmission/reception circuit TRC and the probe connected to the second connection section of the probe connection circuit PCC. The display unit DIS includes first and second CRTs.

Figure 2A:
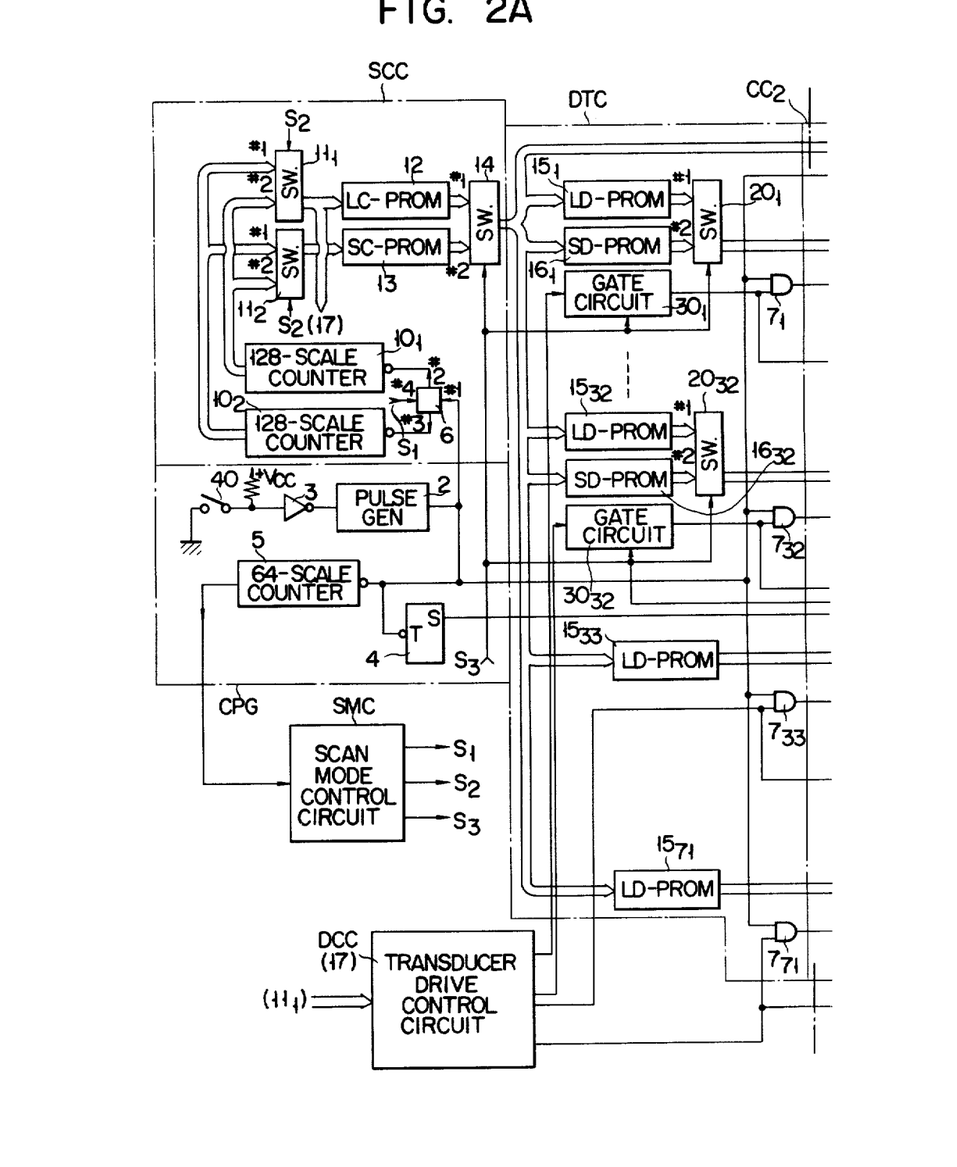
FIGS. 2A, 2B and 2C show a schematic representation of the main configuration of one embodiment of the ultrasonic diagnosing apparatus according to the invention.
Figure 2B:
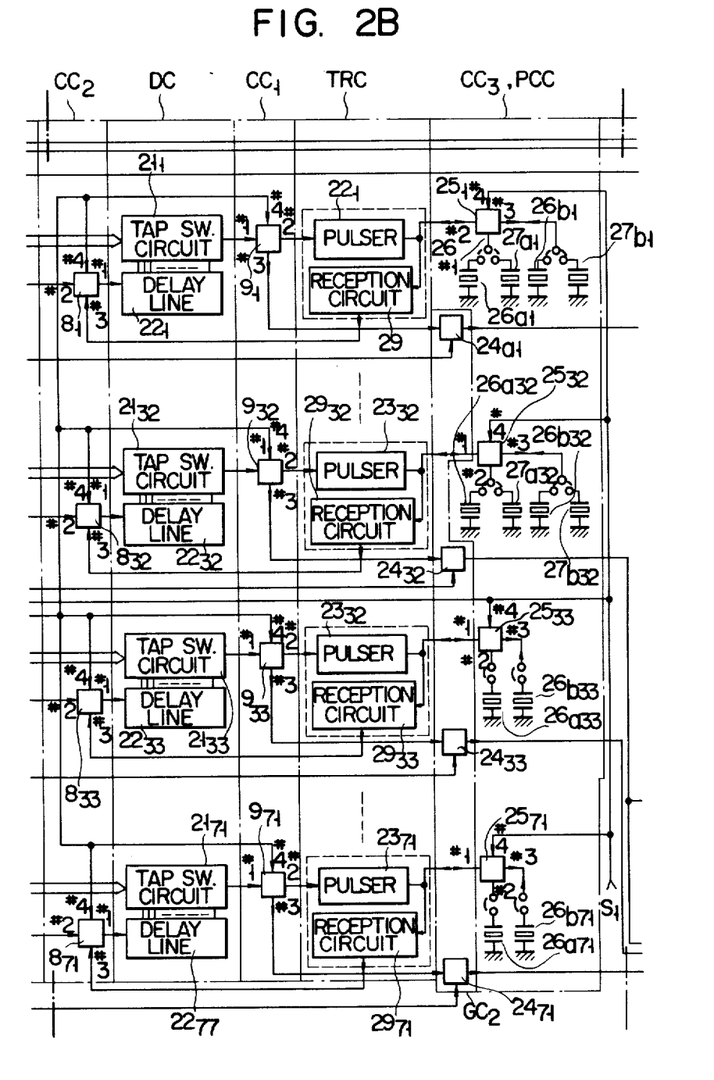
Figure 2C:
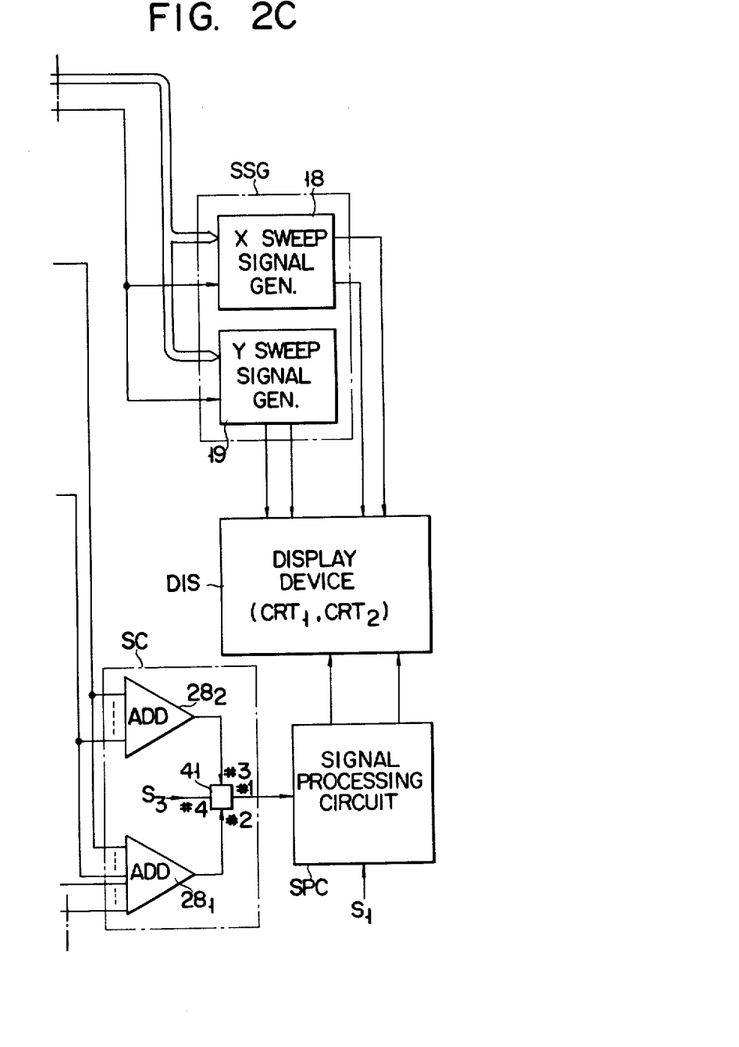

FIGS. 2A, 2B and 2C show a specific configuration of the main portion of the system. Portions enclosed by dot-dash lines correspond to the blocks of FIG. 1 denoted by the same reference symbols as those used in FIG. 2. Reference numeral 2 within the CPG pulse generator denotes a pulse generator with a control terminal. It produces a pulse signal at a repetition frequency of, for instance, 4 kHz (i.e., with the repetition period of 250 μsec.). Its control terminal is connected through an inverter 3 to a start switch 40, and its output terminal is connected to a trigger input terminal of a mono-stable multi-vibrator 4, a count input terminal of a scale-of-64 counter 5, a first terminal of a select switch 6, a first input terminal of of AND gates $7_1$ to $7_{71}$ and to an each input terminal of an X sweep signal generator circuit 18 and a Y sweep signal generator circuit 19 (FIG. 2C) which will be described later in detail.

The mono-stable multi-vibrator 4 produces a pulse having a duration corresponding to a ultrasonic pulse transmission period to be described later. The scale-of-64 counter 5 is a 1/64 frequency divider which produces pulses synchronized with the field period, and its 1/64 frequency division output terminal is connected to an input terminal of the scan mode control circuit SMC. The select switch 6 is an analog switch using a C-MOS FET or the like having first to fourth terminals. The first and second terminals are connected to each other (this state being hereinafter referred to as a first connection state) when a "1" level signal is impressed upon the fourth terminal, while normally (i.e., when the fourth terminal is at a "0" level) the first and third terminals are connected to each other (this state being hereinafter referred to as the second connection state). The mono-stable multi-vibrator 4 has its output terminal connected to the fourth terminal of each of select switches $8_1$ to $8_{71}$ and $9_1$ to $9_{71}$ (which have the same construction as the select switch 6). To the second and third terminals of the select switch 6 are respectively connected count input terminals of respective first and second scale-of-128 counters $10_1$ and $10_2$. The scale-of-128 counters $10_1$ and $10_2$ are address counters for programmable read only memories for linear and sector electronic scan controls (hereinafter referred to as LC-PROM and SC-PROM respectively) to be described later in detail. The counter $10_1$ has its output terminal connected to a first input terminal of each of switching circuits $11_1$ and $11_2$, and the counter $10_2$ has its output terminal connected to a second input terminal of each of the switching circuits $11_1$ and $11_2$.

The switching circuits $11_1$ and $11_2$ are each a multiplexer consisting of a high speed switch element such as a C-MOS FET, with the first input terminal being connected to the output terminal (this state being hereinafter referred to as a first connection state) when a "1" level signal is impressed upon a control terminal while the second output terminal being connected to the output terminal (this state being referred to as the second connection state) when the control signal is at a "0" level. Their output terminals are respectively connected to address input terminals of the LC-PROM 12 and SC-PROM 13. The LC-PROM 12 and SC-PROM 13 are controlled by the respective first and second scale-of-128 counters $10_1$ and $10_2$ to produce binary output signals for odd field addresses (1, 3, 5, . . . , 127) and even field addresses (2, 4, 6, . . . , 128) for the individual scan controls. Their binary output terminals are connected to respective first and second output terminals of a switching circuit 14 (which is similar in construction to the switching circuits $11_1$ and $11_2$). The switching circuit 14 has its binary output terminal connected to address input terminals of delay time control programmable read only memories $15_1$ to $15_{71}$ for the aforementioned small angle sector scanning and electronic focusing at the time of the L mode (hereinafter referred to as LD-PROM), delay time control programmable read only memories $16_1$ to $16_{32}$ for the sector scanning and electronic focusing at the time of the S mode (hereinafter referred to as SD-PROM) and X and Y sweep signal generator circuits 18 and 19.

The first LD-PROM $15_1$ and $16_1$ have their binary output terminals connected to respective first and second input terminals of a switching circuit $20_1$ (similar in construction to the switching circuit 14). Likewise, the first to thirty-second LD-PROMs $15_1$ to $15_{32}$ and SD-PROMs $16_2$ to $16_{32}$ have their output terminals connected to first and second input terminals of corresponding switching circuits $20_1$ to $20_{32}$. The switching circuits $20_1$ to $20_{32}$ have their output terminals connected to respective address input terminals of first to thirty-second tap switching circuits $21_1$ to $21_{32}$. The thirty-third to seventy-first LD-PROMs $15_{33}$ to $15_{71}$ have their output terminals connected to address input terminals of respective thirty-third to seventy-first tap switching circuits $21_{33}$ to $21_{71}$. In each of the tap switching circuits $21_1$ to $21_{71}$, a group of analog switches (for instance C-MOS FETs) is on-off controlled according to the address signal input, these analog switches being connected to respective taps of each of LC delay lines $22_1$ to $22_{71}$.

Each of the delay lines $22_1$ to $22_{71}$ has its input terminal connected to the first terminal of each of the select switches $8_1$ to $8_{71}$ and its output terminal connected through each of the tap switching circuits $21_1$ to $21_{71}$ to each of the select switches $9_1$ to $9_{71}$. The select switches $9_1$ to $9_{71}$ each have the second terminal connected to an input terminal of each of pulsers $23_1$ to $23_{71}$ and the third terminal connected to a first input terminal of each of analog switches $24_1$ to $24_7$. The pulsers $23_1$ to $23_{71}$ produce pulse signals necessary for driving transducers to be described later from pulse signals coupled to their input terminals. Their output terminals are each connected to a first terminal of each of select switches $25_1$ to $25_{71}$ (similar in construction to the select switch 6). The select switches $25_1$ to $25_{71}$ each have the second terminal connected to each of first L mode probe transducers $26a_1$ to $26a_{27}$, and the select switches $25_1$ to $25_{32}$ each have the second terminal also connected to each of first S mode probe transducers $27a_1$ to $27a_{32}$. The select switches $25_1$ to $25_{71}$ each have the third terminal connected to each of second L mode probe transducers $26b_1$ to $26b_{71}$, and the select switches $25_1$ to $25_{32}$ each have the third terminal also connected to each of second S mode probe transducers $27b_1$ to $27b_{32}$.

The analog switches $24_1$ to $24_{71}$ have their output terminals each connected to an input terminal of an L mode adder $28_1$, and the analog switches $24_1$ to $24_{32}$ have their output terminals each also connected to an input terminal of an S mode adder $28_2$. The adders $28_1$ and $28_2$ have their output terminals connected to respective first and second terminals of a select switch 41 (similar in construction to the select switch 6). A first terminal of the select switch 41 is connected to an input section of the signal processing circuit SPC which will be described later in detail. The first terminal of each of the select switches $25_1$ to $25_{71}$ is also connected to each of receiving circuits $29_1$ to $29_{71}$. The receiving circuits $29_1$ to $29_{71}$ are pre-amplifiers for adequately amplifying ultrasonic echo signals, and their output terminals are each connected to the third terminal of each of the select switches $8_1$ to $8_{71}$. To the third terminal of each of the select switches $8_1$ to $8_{71}$ is connected the output terminal of each of the AND gates $7_1$ to $7_{71}$. To a second input terminal of each of the AND gates $7_1$ to $7_{32}$ is connected an output terminal of each of the gate circuits $30_1$ to $30_{32}$, and to second input terminals of the AND gates $7_{33}$ to $7_{71}$ are connected respective thirty-third to seventy-first output terminals. The gate circuits $30_1$ to $30_{32}$ have a construction as shown, for instance, in FIG. 3. In this circuit, with a "1" level signal impressed upon a control terminal Tg a signal corresponding to the "1" or "0" level of the input signal to the input terminal Ti appears at the output terminal To, while with a "0" level signal on the control terminal Tg the output at the output terminal To is "1" irrespective of the signal to the input terminal Ti.

Figures 3, 4:
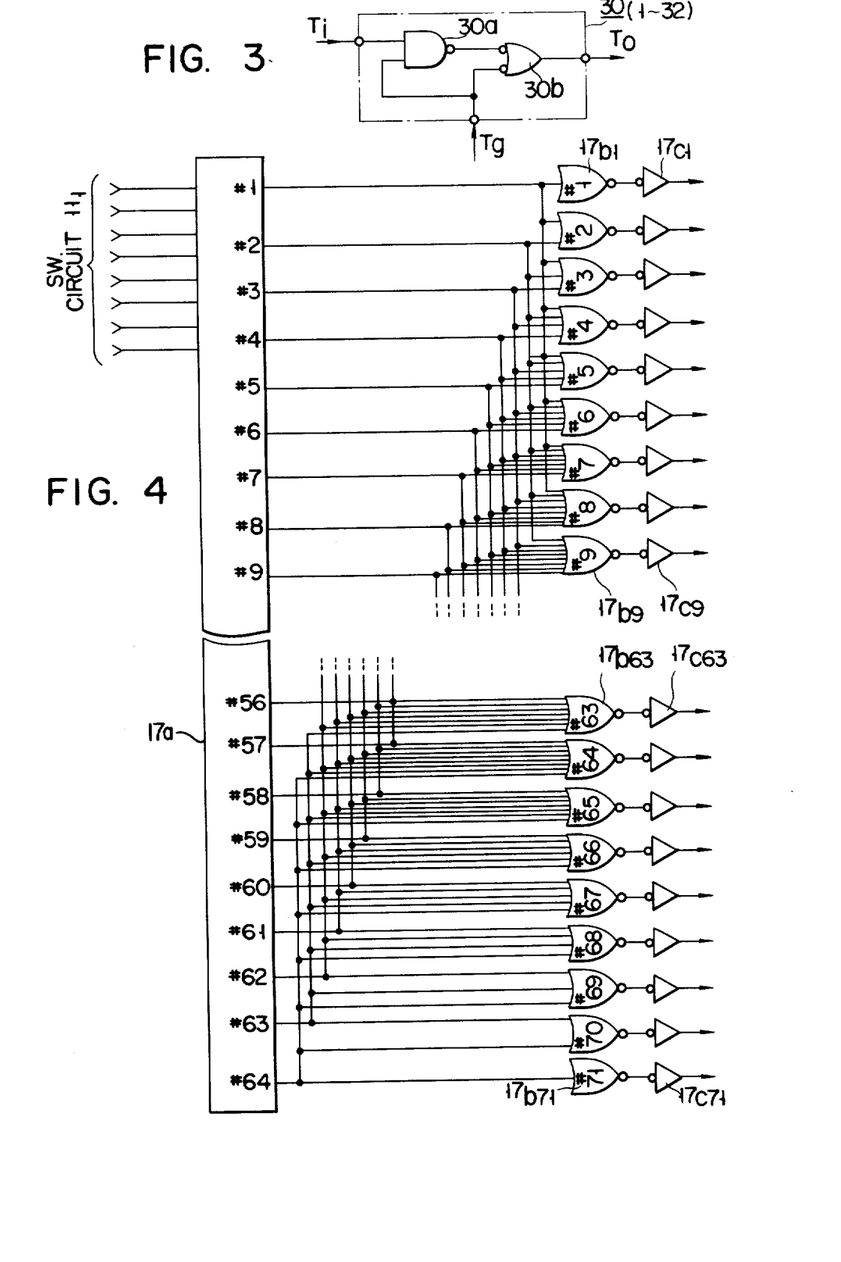
FIG. 3 is a circuit diagram showing a specific construction of gate circuits $30_1$ to $30_{32}$ in the embodiment of FIG. 2.
FIG. 4 is a circuit diagram showing a specific construction of transducer drive control circuit 17 in the embodiment of FIG. 2.

More particularly, in FIG. 3 designated at 30a is a NAND gate having a first input terminal, to which the input terminal Ti is connected, a second input terminal, to which the control terminal Tg is connected, and an output terminal connected to a first input terminal of a NAND gate 30b. The NAND gate 30b has a second input terminal, to which the control terminal Tg is connected, and an output terminal connected to the output terminal To. To the input terminals of the gate circuits $30_1$ to $30_{32}$ are connected respective first to thirty-second output terminals of the transducer drive control circuit 17. The transducer drive control circuit 17 has a construction as shown, for instance, in FIG. 4.

More particularly, as shown in FIG. 4 it comprises a decoder 17a, which has an address input terminal connected to the binary output terminal of the switching circuit $11_1$ and output terminals corresponding in number to the number of (sixty-four) scanning lines constituting one field at the time of the L mode and produces a "1" level signal from an output terminal corresponding to the decimal number represented by the binary signal input to the address input terminal, NOR gates $17b_1$ to $17b_{71}$ corresponding in number to the L mode probe transducers and inverters $17c_1$ to $17c_{71}$ each having an input terminal connected to the output terminal of each of the NOR gates $17b_1$ to $17b_{71}$ and an output terminal constituting an output terminal of the transducer drive control circuit 17. In the decoder 17a, the first output terminal (1) is connected to the input terminals of the first to eighth NOR gates $17b_1$ to $17b_8$, the second output terminal (2) is connected to first or second input terminals of the second to ninth NOR gates $17b_2$ to $17b_9$, and likewise the i-th (i=1, 2, 3, . . . , 64) output terminal is connected to first or second input terminals of the i-th to (i+7)-th NOR gates.

Figure 5:
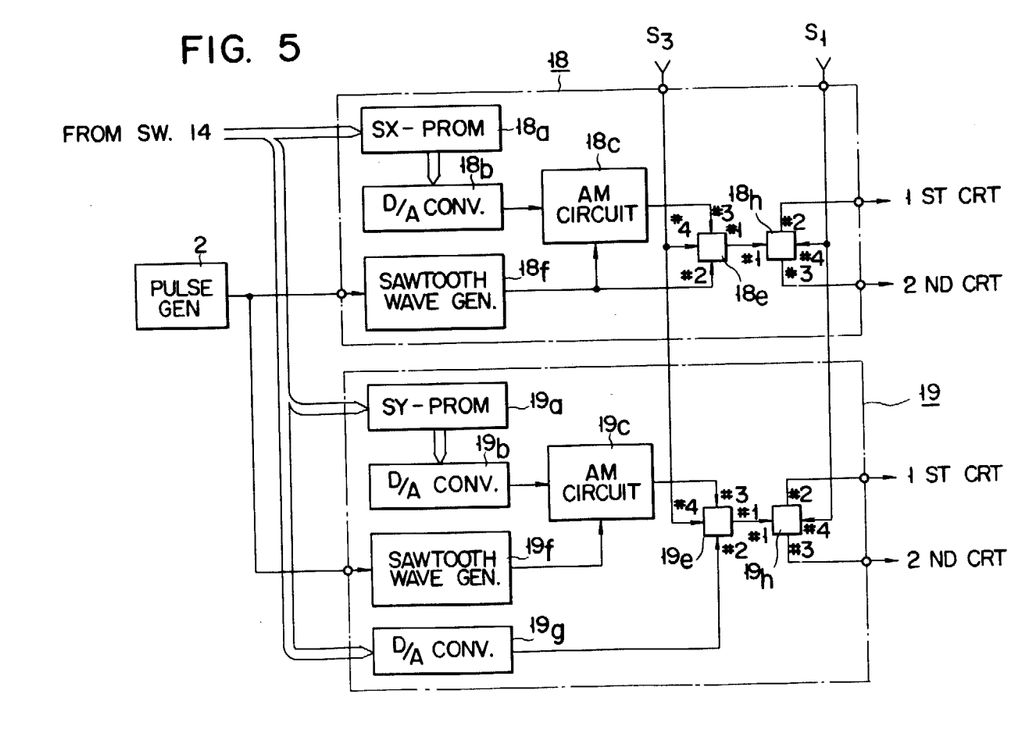
FIG. 5 is a schematic diagram showing specific constructions of X and Y sweep signal generator circuits 18 and 19 in the embodiment of FIG. 2.

FIG. 5 shows the circuit arrangement of the X and Y sweep signal generator circuits 18 and 19. Designated at 18a and 19a are programmable read only memories for controlling X and Y sweep signals at the time of the S mode (hereinafer referred to respectively as SX-PROM and SY-PROM), and their address input terminals are commonly connected to the output terminal of the switching circuit 14. In the SX-PROM 18a and SY-PROM 19a, values obtained by quantizing respective ranges between sin $90° - \theta/2$ and sin $90° + \theta/2$ and between cos $90° - \theta/2$ and cos $90° + \theta/2$ ($\theta$ being the sector scan angle at the time of the S mode) in 128 steps are successively stored. The SX-PROM 18a and SY-PROM 19a have their binary output terminals connected to input terminals of respective digital-to-analog converters (hereinafter referred to as D/A converter) 18b and 19b. The D/A converters 18b and 19b have their output terminals connected to amplitude control (modulating) signal input terminals of respective amplitude modulation circuits 18c and 19c. Designated at 18f and 19f are sawtooth wave generator circuits with input terminals thereof connected to an output terminal of the afore-mentioned pulse generator 2. Their output terminals are connected to modulation input terminals of the respective amplitude modulation circuits 18c and 19c. In the X sweep signal generator circuit 18a, the sawtooth wave generator circuit 18f and amplitude modulation circuit 18c have their output terminals connected to respective second and third terminals of a select switch 18e (similar in construction to the select switch 6). A first terminal of the select switch 18e is connected to a first terminal of a select switch 18h (similar in construction to the select switch 6), which has its second and third terminals connected to the respective first and second CRTs in the CRT display unit DIS. In the Y sweep signal generator circuit 19, a D/A converter 19g with an input terminal thereof connected to the output terminal of the switching circuit 14 is connected to a second terminal of a select switch 19e (similar in construction to the select switch 6). The amplitude modulation circuits 18c and 19c have their output terminals each connected to a third terminal of each of the select switches 18e and 19e. A first terminal of the select switch 19e is connected to a first terminal of a select switch 19h (similar in construction to the select switch 6), which has its second and third terminals connected to the respective first and second CRTs in the CRT display unit DIS.

Figure 6:
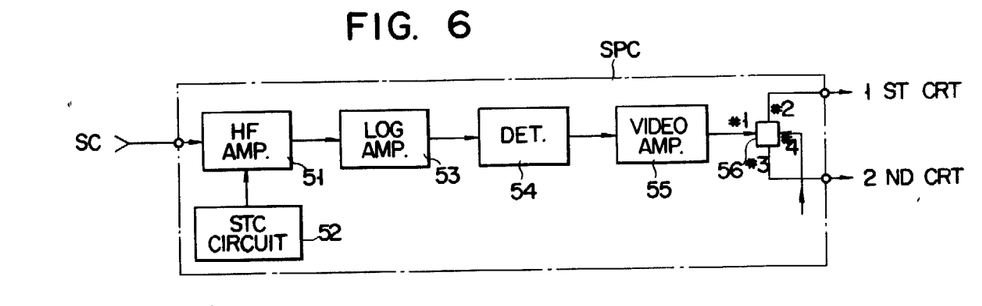
FIG. 6 is a schematic diagram showing a specific construction of signal processing circuit SPC in the embodiment of FIG. 2.

FIG. 6 shows the specific configuration of the signal processing circuit SPC. Its output terminal is connected to an output terminal of the summing circuit SC, i.e., a first terminal of a switching circuit 41, and it includes a high frequency amplifier 51 with the gain thereof adequately controlled by a sensitivity time control circuit 52, a logarithmic amplifier circuit 53 for effecting logarithmic amplification of the output signal of the high frequency amplifier 51, a detecting circuit 54 for detecting the output signal of the logarithmic amplifier 53, a video amplifier circuit 55 for amplifying the output signal of the detecting circuit 54 to produce a video signal for display on a CRT monitor and a select switch 56 (similar in construction to the select switches 18h and 19h) for selectively coupling the output signal of the video amplifier circuit 55 to either one of two CRT systems. The select switch 56 has its second and third terminals connected to the cathode of respective first and second CRTs CRT$_1$ and CRT$_2$ in the CRT display unit DIS in the succeeding stage and its fourth terminal connected to a first output terminal of the scan mode control circuit SMC, from which the first scan mode control signal S$_1$ is produced.

Figures 7, 8:
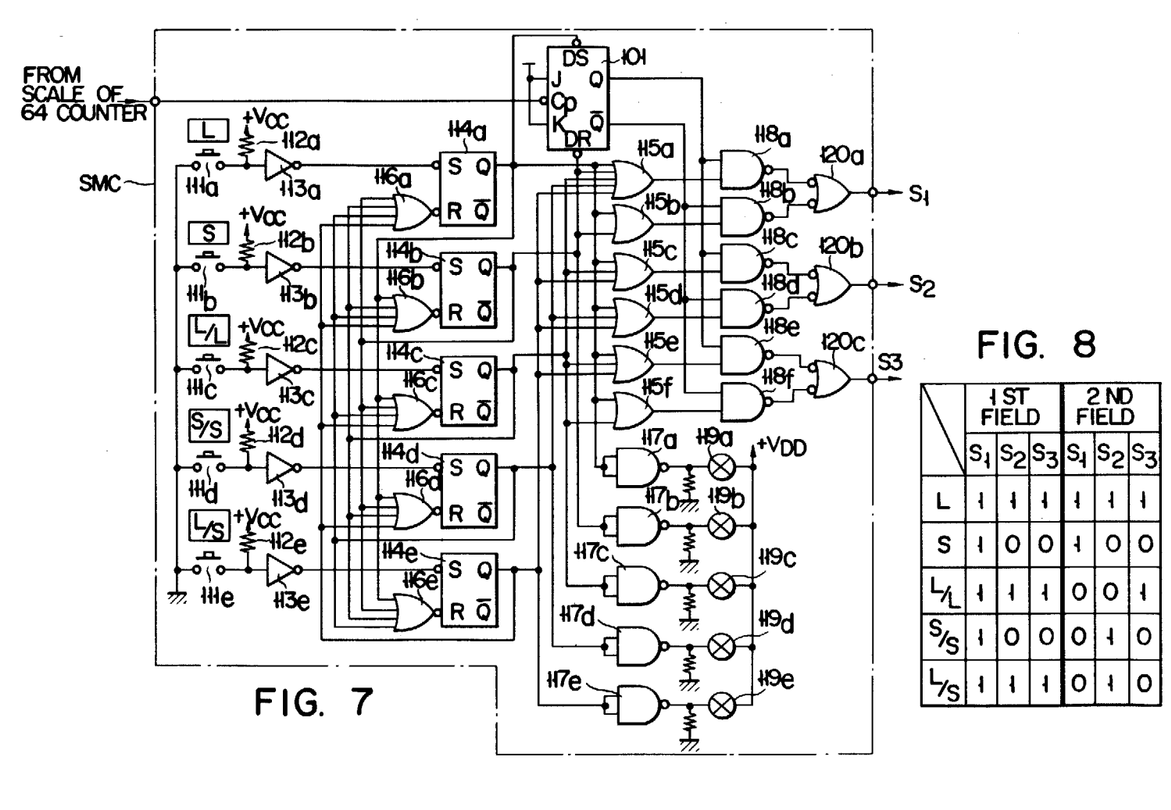
FIG. 7 is a circuit diagram showing a specific construction of scan mode control circuit SMC in the embodiment of FIG. 2.
FIG. 8 is a table showing the signal levels of scan mode control signals $S_1$ to $S_3$ in scan mode control circuit SMC in the embodiment of FIG. 2.

The scan mode control circuit SMC has the specific construction as shown in FIG. 7. Designated at 101 is a J-K flip-flop capable of direct setting and resetting. Its J and K input terminals are both held at a level "1", and its clock pulse input terminal is connected to the 1/64 frequency division output terminal of the scale-of-64 counter 5. Designated at 111a to 111e are scan mode selection switches of the pushbutton type each having one end grounded and the other end connected to each of pull-up resistors 112a to 112e to a power supply V$_{cc}$ and also to an input terminal of each of inverters 113a to 113e. The inverters 113a to 113e have their output terminals each connected to a set terminal of each of first to fifth R-S flip-flops 114a to 114e. The first R-S flip-flop 114a has its Q output terminal connected to a direct set terminal of the J-K flip-flop 101, a first input terminal of each of OR gates 115a to 115f, a first input terminal of each of NOR gates 116b to 116e and to a NAND gate 117a for driving a lamp. The second R-S flip-flop 114b has its Q output terminal connected to a direct reset terminal of the J-K flip-flop 101, a second input terminal of each of the OR gates 115a to 115f, a first input terminal of a NOR gate 116a, a second input terminal of each of the NOR gates 116c to 116e and to a NAND gate 117b for driving a lamp. The third R-S flip-flop 114c has its Q output terminal connected to a third input terminal of the OR gate 115a, a second input terminal of each of the OR gates 115c to 115f, a second input terminal of each of the NOR gates 116a and 116b, a third input terminal of each of the NOR gates 116d and 116e and to a NAND gate 117c for driving a lamp. The fourth R-S flip-flop 114d has its Q output terminal connected to a fourth input terminal of the OR gate 115a, a second input terminal of the OR gate 115d, a third input terminal of each of the NOR gates 116a to 116c, a fourth input terminal of the NOR gate 116e and to a NAND gate 117d for driving a lamp. The fifth R-S flip-flop 114e has its Q output terminal connected to a fourth input terminal of each of the NOR gates 116a to 116d. The OR gates 115a to 115f have their output terminals each connected to each of NAND gates 118a to 118f.

The J-K flip-flop 101 has its Q output terminal connected to a second input terminal of each of the NAND gates 118a, 118c and 118e and its $\overline{Q}$ output terminal connected to a second input terminal of each of the NAND gates 118b, 118d and 118f. The NAND gates 117a to 117e have their output terminals connected to respective lamps 119a to 119e for displaying the selected mode. The NAND gates 118a, 118c and 118e have their output terminals each connected to a first input terminal of each of NAND gates 120a to 120c, and the NAND gates 118b, 118d and 118f have their output terminals each connected to a second input terminal of each of the NAND gates 120a to 120c. The output terminals of the NAND gates 120a to 120c constitute the respective output terminals of the scan mode control circuit 1, from which the first to third scan mode control signals S$_1$ to S$_3$ are provided. The output terminal for the first scan mode control signal S$_1$ is connected to the fourth terminal of each of the select switches 6, 18h, 19h, 25$_1$ to 25$_{71}$ and 56. The output terminal for the third scan mode control signal S$_3$ is connected to the switching circuits 14, 20$_1$ to 20$_{32}$ and select switches 18e, 19e and 41.

Figure 9:
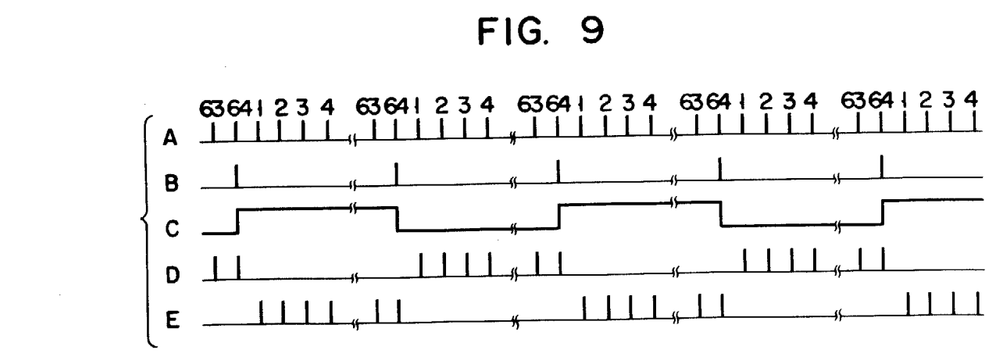
FIG. 9 is a waveform diagram illustrating the operation of the embodiment shown in FIGS. 2 through 7.

The operation of the above configuration will now be described with reference to FIGS. 8 and 9.

In the first place, the operation will be described in connection with the case of the ordinary L mode using a single L mode probe. In this case, the (seventy-one) first L mode probe transducers, 26$a_1$ to 26$a_{71}$ are connected to the second terminal of the respective select switches 25$_1$ to 25$_{71}$.

Then, the switch 111a in the scan mode control circuit SMC in FIG. 7, for selecting the L mode, is closed. As a result, the first R-S flip-flop 114a is set through the inverter 113a, thus causing a lamp 119a to be turned on through the lamp drive NAND gate 117a to indicate that the system operates in the L mode. With the setting of the flip-flop 114a, the J-K flip-flop 101 is directly set, and also the OR gates 115a to 115f each produce a "1" level output. Thus, the NAND gates 118b, 118d and 118f each produce a "0" level output, while the NAND gates 118b, 118d and 118f each produce a "1" level output. Consequently, the outputs of the NAND gates 120a to 120c, i.e., the first to third mode control signals S$_1$ to S$_3$, all become "1". (See a row labeled L in a table of FIG. 8.)

In the above set state, by closing the start switch 40, the pulse generator 2 is caused to start oscillation and produce an output pulse signal (as shown in A in FIG. 9), which is coupled through the select switch 6 to the first scale of 128 counter 10$_1$. As the first scale of 128 counter 10$_1$ counts the input pulses, its binary output value is progressively increased to "1", "2", "3", ..., "128∞", and these values are supplied as address signals through the switching circuit 11$_1$ to the LC-PROM 12. With the output of the scale of 128 counter 10$_1$ supplied as address signal to it, the LC-PROM 12 produces binary values corresponding to odd numbers "1", "3", "5", ..., "127" for the first half of the address signal consisting of addresses "1", "2", "3", ..., up to "64" and produces binary values corresponding to even numbers "2", "4", "6", ..., "128" for the second half of the address signal consisting of addresses "65", "66", "67", ..., up to "128". The output signal of the LC-PROM 12 is successively coupled as address signal through the switching circuit 14 to the first to seventy-first LD- PROM $15_1$ to $15_{71}$, while also the output signal of the first scale of 128 counter $10_1$ is coupled as successive address signals through the switching circuit $11_1$ to the decoder $17a$ of the transducer drive control circuit 17. In the transducer drive control circuit 17 shown in FIG. 4, the decoder $17a$ is thus addressed by the output signal of the first scale of 128 counter $10_1$ so that the output terminals (1) to (63) of the decoder $17a$ are successively brought to "1"level. Thus, the NOR gates $17b_1$ to $17b_{71}$ are successively brought to "0" level eight NOR gates at a time, that is, the first to eighth NOR gates $17b_1$ to $17b_8$ at first, then the second to ninth NOR gates $17b_2$ to $17b_9$ and then the third to tenth NOR gates $17b_3$ to $17b_{10}$ and so on and the sixty-fourth to seventy-first NOR gates $17b_{64}$ to $17b_{71}$ at last, so that the output terminals 1 to 71 of the transducer drive control circuit 17 are successively brought to "1" level eight of them at a time, that is, the output terminals 1 to 8 at first, then 2 to 9 and then 3 to 10 and so on and 64 to 71 at last, through the inverters $17c_1$ to $17c_{71}$.

Thus, the input terminals of the gate circuits $30_1$ to $30_{32}$ are successively brought to "1" level eight of them at a time, that is, gate circuits $30_1$ to $30_8$ at first, then $30_2$ to $30_9$ and then $30_3$ to $30_{10}$ and so on and $30_{24}$ to $30_{32}$ at last, thus successively bringing the second input terminals of the AND gates $7_1$ to $7_{71}$ to "1" level. At this time, the output of the individual gate circuits $30_1$ to $30_{32}$ is brought to the same "1" level as the input. More particularly, since the first scan mode signal $S_1$ is at "1" level, the control terminal Tg in FIG. 3 is at "1" level, and thus with the input terminal Ti brought to "1" level the output of the NAND gate $30a$ is brought to "0" level so that the output of the NAND gate $30b$, i.e., the output of the gate circuit, is brought to "1" level. Thus, the output pulses of the pulse generator 2 are sequentially passed through the AND gates $7_1$ to $7_{71}$ eight thereof at a time, that is, through the AND gates $7_1$ to $7_8$ at first, then $7_3$ to $7_{10}$ and then $7_5$ to $7_{12}$ and so on and eventually $7_{63}$ to $7_{70}$, then $7_2$ to $7_9$, then $7_4$ to $7_{11}$ and then $7_6$ to $7_{13}$ and so on and $7_{64}$ to $7_{71}$ at last, and further through the select switches $8_1$ to $8_{71}$ in same manner as for the AND gates $7_1$ to $7_{11}$ to the corresponding select switches $8_1$ to $8_{71}$.

Meanwhile, with the outputs of the LD-PROMs $15_1$ to $15_{71}$ the tap switching circuits $21_1$ to $21_{71}$ are sequentially addressed eight of them at a time to effect tap switching control of the corresponding delay lines $22_1$ to $22_{71}$. The pulse signal from the pulse generator 2 is thus adequately delayed by the delay lines $22_1$ to $22_{71}$ and coupled through the select switches $9_1$ to $9_{71}$ to the pulsers $23_1$ to $23_{71}$ for adequate voltage amplification therein, and are then coupled through the select switches $25_1$ to $25_{71}$ to the L mode probe transducers $26a_1$ to $26a_{71}$. Thus, the transducers $26a_1$ to $26a_{71}$ are sequentially driven eight of them at a time, that is, the transducers $26a_1$ to $26a_8$ at first, then $26a_3$ to $26a_{10}$ and then $26a_5$ to $26a_{12}$ and so on and eventually $26a_{63}$ to $26a_{70}$, then the transducers $26a_2$ to $26a_9$, then $26a_4$ to $26a_{11}$ and then $26a_6$ and $26a_{13}$ and so on and $26a_{64}$ to $26a_{71}$ at last. In this way, consecutive phase differences are provided in the timing of the driving of the transducers $26a_1$ to $26a_{71}$ which are apparently driven all at a time but are actually driven eight of them at a time by the delay lines $22_1$ to $22_{71}$ such that a small angle of $+0.46$ degree is provided by each odd number address and $-0.46$ degree by each even number address and also that adequate electronic focusing is effected.

With the transducers $26a_1$ to $26a_{71}$ thus driven eight of them at a time, sixty-four successive ultrasonic beams each having the small angle of $+0.46$ degree are obtained from the sixty-four transducers as the first scale of 128 counter $10_1$ counts "1" up to "64" (i.e., during the first or odd field) and another sixty-four successive beams each having the small angle of $-0.46$ degree are obtained from these sixty-four transducers as the counter counts "64" up to "128" (i.e., during the second or even field), that is, a total of one hundred and twenty-eight successive beams (constituting one frame) are obtained, these beams being projected into the probed body.

The ultrasonic beams thus projected into the probed body are reflected according to the acoustic impedance among the tissues of the body and are returned as ultrasonic echoes to the transducers $26a_1$ to $26a_{71}$. These ultrasonic echoes are sequentially received eight echoes as one set which is the same as that at the time of the projection, and are coupled through the select switches $25_1$ to $25_{71}$ to the receiving circuits $29_1$ to $29_{71}$.

Meanwhile, the select switches $8_1$ to $8_{71}$ and $9_1$ to $9_{71}$ are held in a state with the first and second terminals connected to each other, for a period corresponding to the duration of the output pulse from the mono-stable multi-vibrator 4 which is triggered by the output pulse of the pulse generator 2, i.e., for the period of transmission of ultrasonic beams. This means that these select switches are held in an ordinary state with the first and third terminals connected to each other at the time when the afore-mentioned ultrasonic echoes are received. Thus, the ultrasonic echoes led to the receiving circuits $29_1$ to $29_{71}$ are adequately amplified there and then fed back through the select switches $8_1$ to $8_{71}$ to the delay lines $22_1$ to $22_{71}$ to be delayed there under the same condition as at the time of the transmission before they are sequentially coupled through the analog switches $24_1$ to $24_{71}$ to the first to seventy-first input terminals of the L mode adder $28_1$. The analog switches $24_1$ to $24_{71}$ are controlled (i.e., on-off operated) according to the output level of the first to seventy-first outputs of the transducer drive control circuit 17, so that in effect they function to supply only the ultrasonic echo signals received by the same (eight) transducers as at the time of the transmission to the succeeding stage adder $28_1$. Thus, when the ultrasonic beams projected from a set of eight transducers are returned as respective ultrasonic echoes, there is no possibility of picking up noise echo signals received by other transducers than in that set.

Meanwhile, the pulse signal of the pulse generator 2 (as shown in A in FIG. 9) is coupled to the X and Y sweep signal generator circuits 18 and 19 to produce X and Y sweep signals for the L mode. In FIG. 5, the pulse output of the pulse generator 2 is coupled to the sawtooth wave generator circuits $18f$ and $19f$ of the respective X and Y sweep signal generator circuits 18 and 19. The sawtooth wave generator circuits $18f$ and $19f$ produce sawtooth waves having a constant slope and a constant amplitude covering the pulse repetition period from their pulse input as trigger signal, and these sawtooth waves are supplied as respective X and Y signals through the select switches $18e$, $19e$, $18h$ and $29h$ to the signal processing circuit SPC. The output of the switching circuit 14 is also coupled to the D/A converter $19g$ of the Y sweep signal generator circuit 19, so that this binary (digital) signal is converted into a staircase (analog) signal having a constant slope and a constant amplitude covering the field period. This staircase signal is supplied as Y sweep signal through the select switches 19e and 19h to the CRT display unit DIS.

The ultrasonic echo signals sequentially coupled to the adder $28_1$ are progressively added therein, and are then supplied through the select switch 41 to the signal processing circuit SPC. In the signal processing circuit SPC, the received sum of echo signals is high frequency amplified in the high frequency amplifier 51 (FIG. 6) with the gain adequately controlled according to a gain control signal from the STC circuit 52, then subjected to logarithmic amplification in the detecting circuit 54 and then coupled to the detecting circuit 54 to produce an envelope signal, which is subjected to adequate video amplification in the video amplifier circuit 56 to produce a Z (brightness) signal which is coupled to the first CRT in the CRT display unit DIS. Thus, in the L mode with (64×2) scanning lines for one frame (i.e., two fields) a tomogram of the probed area of the body is displayed on the first CRT.

The operation will now be described in connection with the case of the ordinary S mode using a single S mode probe. In this case, the (thirty-two) first S mode probe transducers $27a_1$ to $27a_{32}$ are connected to the third terminal of the respective select switches $25_1$ to $25_{32}$ (FIG. 2B).

Then, the switch 111b in the scan mode control circuit SMC in FIG. 7, for selecting the S mode, is closed. As a result, the second R-S flip-flop 114b is set through the inverter 113b to reset the other R-S flip-flops 114a and 114c to 114e, which have been in the set state, through the respective NOR gates 116a and 116c to 116e and turn off the corresponding scan mode display lamps 119a and 119c to 119e. At the same time, the lamp 119b is turned on through the lamp drive NAND gate 117b to indicate that the system operates in the S mode (the second scan mode), and the J-K flip-flop 101 is directly set as well as inverting the outputs of the OR gates 115a and 115b to "1". Thus, the Q and $\bar{Q}$ outputs of the J-K flip-flop 101 respectively become "0" and "1", so that among the NAND gates 118a to 118f only the NAND gate 118a produces "1" level output, the other NAND gates all producing "0" level output. This means that in this case the first to third scan mode control signals $S_1$ to $S_3$ are respectively "1", "0" and "0". (See a row labeled S in the table of FIG. 8.) Thus, the switching circuits $11_1$, $11_2$, 14, $20_1$ to $20_{32}$, which are set to the state with the first input terminal connected to the output terminal in the case of the L mode, are this time set to the state with the second input terminal connected to the output terminal. Likewise, the select switches 18e, 19e (FIG. 5) and 41 (FIG. 2C), which are set to the state with the first and third terminals connected to each other in the case of the L mode, are set to the state with the second and third terminals connected to each other. Further, since the control terminal Tg of each of the gate circuits $30_1$ to $30_{32}$ is set to "0" level, the output of the NAND gate 30b, i.e., the output of each gate circuit, is set to "1" level.

By closing the start switch 40 in the above set state, the output pulse signal of the pulse generator 2 (as shown in A in FIG. 9) is coupled through the select switch 6 to the scale of 128 counter $10_1$. Thus, the binary output value of the scale of 128 counter $10_1$ is progressively increased to "1", "2", "3", . . . , "128" as described earlier and supplied as address signal through the switching circuit $11_2$ to the SC-PROM 13. With the output of the scale of 128 counter $10_1$ supplied as address signal to it, the SC-PROM 13 produces binary values corresponding to odd numbers "1", "3", "5", . . ., "127" for the first half of the address signal consisting of addresses "1", "2", "3", . . ., up to "64" and produces binary values corresponding to even numbers "2", "4", "6", . . ., "128" for the second half of the address signal consisting of addresses "65", "66", "67", . . . , up to "128". The output signal of the SC-PROM 13 is successively coupled as address signal through the switching circuit 14 to the first to thirty-second SD-PROMs $16_1$ to $16_{32}$ and also to the X and Y sweep signal generator circuits 18 and 19.

The output pulses of the pulse generator 2 are coupled through the AND gates $7_1$ to $7_{73}$ and select switches $8_1$ to $8_{32}$ to the delay lines $22_1$ to $22_{32}$ at the same timing. Meanwhile, with the outputs of the SC-PROMs $16_1$ to $16_{32}$ the tap switching circuits $21_1$ to $21_{32}$ are addressed to effect tap switching control of the delay lines $22_1$ to $22_{32}$. The pulse signal from the pulse generator 2 is thus adequately delayed by the delay lines $22_1$ to $22_{32}$ and coupled through the select switches $9_1$ to $9_{32}$ to the pulsers $23_1$ to $23_{32}$ for adequate voltage amplification therein, and are then coupled through the select switches $25_1$ to $25_{32}$ to the S mode probe transducers $27a_1$ to $27a_{32}$. At this time, sequential phase differences are provided in the timing of the driving of the thirty-two transducers $27a_1$ to $27a_{32}$, which are apparently driven all at one time, by the delay lines $22_1$ to $22_{32}$ such that sector angles $\theta_1$, $\theta_3$, $\theta_5$, . . . , $\theta_{127}$ are provided by odd number addresses from the SD-PROMs $16_1$ to $16_{32}$ and sector angles $\theta_2$, $\theta_4$, $\theta_6$, . . . , $\theta_{128}$ from even number addresses and also that adequate electronic focusing is provided.

In the above way, the transducers $27a_1$ to $27a_{32}$ are apparently simultaneously driven, and sixty-four successive ultrasonic beams having the respective odd number sector angles $\theta_1$, $\theta_3$, $\theta_5$, . . . , $\theta_{128}$ are obtained as the first scale of 128 counter $10_1$ counts "1" to "64" (i.e., during the first or odd field) while obtaining another sixty-four successive beams with the respective even number sector angles $\theta_2$, $\theta_4$, $\theta_6$, . . . , $\theta_{128}$ as the counter counts "65" to "128" (i.e., during the second or even field), that is, a total of one hundred and twenty-eight successive beams are obtained, these beams being projected into the probed body.

Like the case of the L mode as mentioned earlier, the ultrasonic echo signals led to the receiving circuits $29_1$ to $29_{32}$ are adequately amplified therein and then coupled through the select switches $8_1$ to $8_{32}$ to the delay lines $22_1$ to $22_{32}$ to be delayed therein under the same condition as at the time of the transmission before they are sequentially coupled through the analog switches $24_1$ to $24_{32}$ to the first to thirty-second input terminals of the S mode adder $28_2$.

Meanwhile, the output of the SC-PROM 13 is coupled to the X and Y sweep signal generator circuits 18 and 19 to produce X and Y sweep signals for the S mode in co-operation with the pulse signal from the pulse generator 2 and the binary signal from the second scale of 128 counter $10_2$. More particularly, in FIG. 5, in the X sweep signal generator circuit 18 binary values produced by quantizing the afore-mentioned sine and cosine curves corresponding to the sector angles $\theta_1$ to $\theta_{128}$ in 128 steps according to the address signal are obtained from the SX-PROM 18a and SY-PROM 19a. These binary signals are converted by the D/A converters 18b and 19b into corresponding analog signals which are supplied as modulating signal to the amplitude modulation circuits 18c and 19c. Thus, the aforementioned sawtooth waves having a constant slope and a constant amplitude produced from the sawtooth wave generator circuits 18f and 19f are amplitude modulated with the modulating signal in the amplitude modulation circuits 18c and 19c. The output signals of the amplitude modulation circuits 18c and 19c are supplied through the select switches 18e, 19e, 18h and 19h to the signal processing circuit SPC.

The ultrasonic echo signals sequentially coupled to the adder $28_2$ are progressively added therein, and are then subjected to the afore-mentioned processing in the signal processing circuit SPC to produce a Z (brightness) signal which is supplied to the first CRT in the CRT display unit DIS. Thus, in the S mode with (64×2) scanning lines (i.e., two fields) a tomogram of the probed area of the body is displayed on the first CRT.

Now, the operation will be described in connection with the case of the L/L mode, in which tomograms of two different portions are displayed on a time-division basis by using two L mode probes. In this case, the first and second L mode probe transducers $26a_1$ to $26a_{71}$ and $26b_1$ to $26b_{71}$ are connected to the second and third terminals of the respective select switches $25_1$ to $25_{71}$.

Then, the switch 111c in the scan mode control circuit SMC in FIG. 7, for selecting the L/L mode, is closed. As a result, the third flip-flop 114c is set through the inverter 113c while the other R-S flip-flops are all reset. At this time, only a lamp 119c is turned on through the lamp drive NAND gate 117c to indicate that the system operates in the L/L mode. At this time, the direct set terminal (DS) and direct reset terminal (DR) of the J-K flip-flop 101 are both set to "1" level, so that the Q and $\overline{Q}$ outputs of the J-K flip-flop 101 are alternately inverted to "1" and "0" every time a 1/64 frequency division output pulse (as shown in B in FIG. 9) is coupled (for each field period) to the clock pulse input terminal (Cp) (as shown in C in FIG. 9). Also, with the setting of the third R-S flip-flop 114c, the outputs of the OR gates 115a, 115c, 115e and 115f all become "1", while the outputs of the OR gates 115b and 115d both become "0". With the "1" level Q output and "0" level $\overline{Q}$ output of the J-K flip-flop 101 the outputs of the NAND gates 118a, 118c and 118e are all at "0" level, while the outputs of the NAND gates 118b, 118d and 118f are all at "1" level. Consequently, the outputs of the NAND gates 120a to 120c, i.e., the scan mode control signals $S_1$ to $S_3$, become "1", which is the same as in the L mode described above. With the "0" level Q output and "1" level $\overline{Q}$ output of the J-K flip-flop 101 the outputs of the NAND gates 118a to 118e are all "1" while the output of the NAND gate 118f is "0". Consequently, the outputs of the NAND gates 120a to 120c, i.e., the scan mode control signals $S_1$ to $S_3$, respectively become "0", "0" and "1". (See a row labeled L/L in the table of FIG. 8.)

By closing the start switch 40 when the J-K flip-flop 101 is in the state with the Q and $\overline{Q}$ outputs being respectively "1" and "0" (hereinafter referred to as set output level state), the output pulse signal of the pulse generator 2 (as shown in A in FIG. 9) is coupled through the select switch 6 to the first scale of 128 counter $10_1$ and counted therein. While the counter $10_1$ counts "1" to "64", the same operation as for the odd field at the time of the L mode is obtained. During this period, the same video signals (X, Y and Z signals) as for the odd field at the time of the L mode are obtained through the first L mode probe consisting of the transducers $26a_1$ to $26a_{71}$ each connected to the second terminal of each of the select switches $25_1$ to $25_{71}$. At this time, pulses as shown in D in FIG. 9 are coupled to the first scale of 128 counter $10_1$. Thus, the same X and Y sweep signals as those for the odd field at the time of the L mode are coupled from the X and Y sweep signal generator circuits 18 and 19 through the second terminals of the select switches 18h and 19h to the signal processing circuit SPC while also the sum of echo signals is supplied from the L mode adder $28_1$ to the circuit SPC for adequate processing therein, and the output signal thus obtained is supplied as Z (brightness) signal through the second terminal of the select switch 56 to the first CRT of the CRT display unit DIS. When the counting in the first scale of 128 counter $10_1$ proceeds up to "64", another 1/64 frequency division output pulse is produced from the scale of 128 counter 5, the Q and $\overline{Q}$ outputs of the J-K flip-flop 101 in the scan mode control circuit SMC are inverted, with the Q output becoming "0" and the $\overline{Q}$ output becoming "1" (this state being hereinafter referred to as reset output state). At this time, pulses as shown in E in FIG. 9 are coupled to the second scale of 128 counter $10_2$. Also, the first to third scan mode control signals $S_1$ to $S_3$ respectively become "0", "0" and "1". As a result, the select switches 6, 18h, 19h and 56, which have previously been in the state with the first and second terminals connected to each other, are switched to the state with the first and third terminals connected to each other, and also the select circuits $11_1$ and $11_2$ are switched from the previous state with the first input terminal connected to the output terminal to the state with the second input terminal connected to the output terminal.

Thus, the output pulse signal of the pulse generator 2 is coupled through the select switch 6 to the second scale of 128 counter $10_2$, and the binary output thereof is coupled as address signal to the LD-PROM 12. The second scale of 128 counter $10_2$ thus counts "1" to "64", and during this time the same video signals (X, Y and Z signals) as for the odd field at the time of the L mode are obtained through the second L mode probe consisting of the other transducers $26b_1$ to $26b_{71}$ each connected to the third terminal of each of the select switches $25_1$ to $25_{71}$. Thus, the same X and Y sweep signals as for the odd field at the time of the L mode are coupled from the X and Y sweep signal generator circuits 18 and 19 through the third terminals of the select switches 18h and 19h to the signal processing circuit SPC while also the sum of echo signals is supplied from the L mode adder $28_1$ to the circuit SPC for adequate processing therein, and the output signal thus obtained is supplied as Z (brightness) signal through the third terminal of the select switch 56 to the second CRT of the CRT display unit DIS. When another 1/64 frequency division output pulse (as shown in B in FIG. 9) is produced from the scale of 128 counter 5, the Q and $\overline{Q}$ outputs of the J-K flip-flop 101 are again inverted to the respective set output levels. As a result, the connection state of the select switches 6, 18h, 19h and 56 are switched, and the output pulse signal is again coupled to the first scale of 128 counter $10_1$. Thus, the scale of 128 counter $10_1$ is caused to count this time "65" to "128", and the LC-PROM 12 is even number addressed. During this time, the video signals (X, Y and Z signals) for the even field are obtained through the first L mode probe and supplied to the first CRT by the same action as for the even field at the time of the L mode. When another 1/64 frequency division output pulse (as shown in B in FIG. 9) is produced from the scale of 128 counter 5, the select switch 6 is switched again, so that the output pulse signal of the pulse generator 2 is again coupled to the second scale of 128 counter $10_2$. Thus, the second scale of 128 counter $10_2$ is caused to count this time "65" to "128", and during this time the same video signals (X, Y and Z signals) as for the even field at the time of the L mode are obtained through the second L mode probe and supplied to the second CRT.

In the above way, video signals for the odd and even fields similar to those at the time of the L mode are obtained from the first and second L mode probes intermittently, i.e., with the odd or even field signals obtained one field period after the other field signals are obtained from the same probe, so that different L mode tomograms are displayed on the respective first and second CRTs of the CRT display unit DIS on a time division basis.

Now, the operation will be described in connection with the case of the S/S mode, in which tomograms of two different portions are displayed on a time division basis by using two S mode probes. In this case, the first and second S mode probe transducers $27a_1$ to $27a_{32}$ and $27b_1$ to $27b_{32}$ are connected to the first and second terminals of the respective select switches $25_1$ to $25_{32}$.

Then, by closing the switch 111d in the scan mode control circuit SMC in FIG. 7, for selecting the S/S mode, the fourth R-S flip-flop 114d is set to reset all the other R-S flip-flops, and also a lamp 119d is turned on to indicate that the system is in the S/S mode. With the setting of the fourth R-S flip-flop 114d, the J-K flip-flop 101 is made ready for being inverted by the clock pulse input similar to the case of the afore-mentioned L/L mode. Also, the outputs of the OR gates 115a and 115b become "1", and the outputs of the OR gates 115b, 115c, 115e and 115f become "0". Thus, when the J-K flip-flop 101 is in the set output level state, the output of the NAND gate 118a is "0" while the outputs of the NAND gates 118b to 118f are "1". At this time, the outputs of the NAND gates 120a to 120c, i.e., the scan mode control signals $S_1$ to $S_3$, are respectively "0", "0" and "1". When the J-K flip-flop 101 is in the set output level state, the outputs of the NAND gates 118a to 118c, 118e and 118f are "1" while the output of the NAND gate 118d is "0". At this time, the outputs of the NAND gates 120a to 120c, i.e., the scan mode control signals $S_1$ to $S_3$, are respectively "0", "1" and "0". (See a row labeled S/S in FIG. 8.)

Thus, by closing the start switch 40 when the J-K flip-flop 101 is in the set output level state, the output levels of the J-K flip-flop 101 are inverted to switch the state of the select switches 6, 18h and 19h and select circuits $11_1$ and $11_2$ every time the scale of 64 counter 5 produces a 1/64 frequency division output pulse (a pulse for the field period) like the case of the L/L mode described above. Thus, like the case of the L/L mode the output pulse signal of the pulse generator 2 is alternately coupled to the first and second scale of 128 counter $10_1$ and $10_2$ for the field period for each (as shown in D and E in FIG. 9), so that the SC-PROM 13 is odd number and even number addressed for the field period for each.

Thus, like the case of the L/L mode, with the odd number address signal from the first scale of 128 counter $10_1$ video signals similar to those for the odd field at the time of the S mode are obtained through the first S mode probe (consisting of the transducers $27a_1$ to $27a_{32}$) connected to the second terminals of the select switches $25_1$ to $25_{32}$ and are supplied to the first CRT. In the next field period, with the odd number address signal from the second scale of 128 counter $10_2$ video signals also similar to those for the odd field at the time of the S mode are obtained through the second S mode probe (consisting of the transducers $27b_1$ to $27b_{32}$) connected to the third terminals of the select switches $25_1$ to $25_{32}$ and are supplied to the second CRT. In the next field period, with the even number address signal from the first scale of 128 counter $10_1$ video signals similar to those for the even field at the time of the S mode are obtained through the first S mode probe and supplied to the first CRT. In the next field period, with the even number address signal from the second scale of 128 counter $10_1$ video signals similar to those for the even field at the time of the S mode are obtained through the second S mode probe and supplied to the second CRT.

In the above way, video signals for the odd and even fields similar to those at the time of the S mode are obtained from the first and second S mode probes intermittently, i.e., with the odd or even field signals obtained one field period after the other field signals are obtained from the same probe, so that different S mode tomograms are displayed on the respective first and second CRTs of the CRT display unit DIS on a time division basis.

Now, the operation will be described in connection with the case of the L/S mode, in which tomograms of two different portions are displayed on a time division basis by using an L mode probe and an S mode probe. In this case, the L mode probe transducers $26a_1$ to $26a_{71}$ are connected to the second terminals of the select switches $25_1$ to $25_{71}$, and the S mode probe transducers $27a_1$ to $27a_{32}$ are connected to the third terminals of the select switches $25_1$ to $25_{32}$.

Then, the switch 111e in FIG. 7 is closed. As a result, the fifth R-S flip-flop 114e is set to turn on a lamp 119e, thus indicating that the system is in the L/S mode. With the setting of the fourth R-S flip-flop 114e, the J-K flip-flop 101 made such that its Q and $\overline{Q}$ output levels can be inverted with the clock pulse input like the case of the L/L and S/S modes described above. Also, the OR gates 115a and 115c to 115e each provide "1" level output, while the OR gates 115b and 115f each provide "0" level output. Thus, when the J-K flip-flop 101 is in the set output level state, the outputs of the NAND gates 118a, 118c and 118e are "0" while the outputs of the NAND gates 118b, 118d and 118f are "1". At this time, the outputs of the NAND gates 120a to 120c are thus all "1", that is, at this time the scan mode control signals $S_1$ to $S_3$ are the same in level as for the odd field period in the L/L mode. When the J-K flip-flop 101 are in the reset output level state, the NAND gates 118a to 118c, 118e and 118f each provide "1" level output while the NAND gate 118d provides "0" level output. Thus, the outputs of the NAND gates 120a to 120c at this time are respectively "0", "1" and "0", that is, at this time the scan mode control signals $S_1$ to $S_3$ are the same in level as for the even field period in the L/L mode.

By closing the start switch 40 when the J-K flip-flop 101 is in the set output level state, like the case of the L/L and S/S modes the output levels of the J-K flip-flop 101 are inverted to switch the connection state of the select switches 6, 18e, 18h, 19e, 19h, 41 and 56 and select circuits $11_1$, $11_2$, 14 and $20_1$ to $20_{32}$ for every field period. Thus, the LC-PROM 12 and SC-PROM 13 are alternately supplied with intermittent odd and even field address signals each for one field period.

Consequently, the first CRT is supplied with video signals similar to those obtained from the first L mode probe at the time of the L/L mode, and the second CRT is supplied with video signals similar to those obtained from the second S mode probe at the time of the S/S mode.

Thus, two tomograms in the different scan modes, i.e., the L and S modes, are displayed on the respective first and second CRTs on a time division basis.

As has been described above, the ultrasonic diagnosing apparatus according to the invention can be operated in either one of five different scan modes (i.e., L, S, L/L, S/S and L/S modes), so that it can be used in conformity to the portion and purpose of the diagnosis. Thus, it is possible to widely improve the diagnosing capability of the electronic scan type ultrasonic diagnosing apparatus.

More particularly, the L and S modes, like the prior art, permit real time diagnosis of the active state of moving portions of the body such as the abdomen and heart. The L/L mode can make up for the drawback of the L mode. While the L mode is superior in the hardiness and real time display to what is called contact band scan system, in which a probe consisting of a single transducer is manually scanned, in this mode the field of diagnosis is restricted by the probe width and is narrow. By using two L mode probes at one time, it is possible to obtain a wider field of diagnosis than that obtainable in the L mode.

The S/S mode is effective where it is desired to obtain a stereoscopic diagnosis by obtaining two tomograms of, for instance, the heart taken in different directions (for instance in perpendicular directions). In this mode, this is realized by applying the two probes to narrow portions of the body between adjacent ribs.

The L/S mode is very effective for diagnosing the relation between the heart and the pulsation of the main artery in the abdomen. Since in the L mode a wide area can be in contact with the surface of the body, so that it is suited for the diagnosis of abdominal arteries, while the S mode is suited for diagnosing the heart from a narrow place such as a portion between adjacent ribs. Thus, this mode is very effective when observing a tomogram of the heart and a tomogram of the abdomen at the same time.

The afore-described embodiment is by no means limitative, and various changes and modifications can be made without departing from the scope of the invention. For example, while in the above embodiment the X-Y CRT monitors are used as the display unit for displaying to tomograms, it is also possible to make use of the general television monitor by setting the pulse repetition period of the output of the pulse generator to the scanning frequency of the television monitor. Also, the general television monitor can be used by the agency of a commonly termed scan converter. Further, while in the above embodiment the two different tomograms obtained on a time division basis in the L/L, S/S and L/S modes are displayed on the respective independent display monitors, it is of course possible to display the two images side by side on a single CRT monitor by using the well-known 2-channel image display techniques. Further, while in the above embodiment the image of one frame is formed by interlaced scanning, i.e., alternate scanning of the odd and even field, it is also possible to form one frame not by the interlaced scanning, that is, by the consecutive scanning or so-called non-interlaced scanning through appropriate control of the output timing of the first and second scale of 128 counters $10_1$ and $10_2$ or through appropriate changes of the memory contents of the LC-PROM 12 and SC-PROM 13. Further, while the above embodiment adopts what is called an alternate system of switching the period of switching the driving of the first and second probes, i.e., the period of time division of video signals, in the L/L, S/S and L/S modes as the field period, it is also possible to adopt a commonly termed chopper system, in which the switching period is the pulse repetition period of the output of the pulse generator 2. This chopper system can be realized by directly coupling the output pulse signal of the pulse generator 2 as the clock pulse input to the J-K flip-flop 101.

What we claim is:

1. An ultrasonic diagnosing apparatus comprising:
   probe means including a plurality of ultrasonic transducers and means for actuating said transducers to produce ultrasonic scanning beams and to receive the reflections thereof from a subject under examination;
   scan mode selection means for selectively producing either a first or a second scan mode control signal representing either a linear scan mode or a sector scan mode, respectively;
   scanning control means including means for delaying driving timing signals fed to said transducers and the echo signals received thereby, said scanning control means being controlled by said first scan mode control signal to set said delay means to produce a series of parallel scanning beams for linear scanning and being controlled by said second scan mode control signal to set said delay means to produce a series of divergent scanning beams for sector scanning;
   signal processing means responsive to said mode control signals for transforming the echo signals received by said transducers into video signals in accordance with either a linear or a sector scan processing algorithm; and
   display means for displaying at least one tomogram according to said video signals produced by said signal processing means.

2. An ultrasonic diagnosing apparatus according to claim 1, wherein said scanning control means includes:
   first means for storing scanning addresses and producing address signals corresponding to the transducers of said probe means as driven during said linear scanning and said sector scanning operations;
   second means for storing data representing a delay time for each transducer of said probe corresponding to each said address signal; and
   means for selectively controlling said means for delaying driving timing signals and ultrasonic echo signals in accordance with the data stored in said second means.

3. An ultrasonic diagnosing apparatus comprising:
   a control pulse generator circuit for producing a reference control pulse signal for determining a scanning rate, a first period control pulse signal for determining an ultrasonic wave generation period, and a second period control pulse signal determining a linear/sector scanning period, said first and second period control signals being produced on the basis of said reference control pulse signal;

a scan mode control circuit including means for selecting either an electronic linear or sector scan mode by receiving said second period control pulse signal and means for producing a scan select signal for controlling said ultrasonic diagnosing apparatus to effect a selected linear or sector scan;

a scanning control circuit for producing a scanning control signal corresponding to said selected scan mode on the basis of said scan select signal and reference control pulse signal;

a transducer drive control circuit for driving a predetermined number of said transducers in a linear scan probe at one time and successively shifting said transducers driven according to said scanning control signal;

a delay time control circuit for providing transducer drive signals and ultrasonic echo signals with predetermined delay times for sector scan and electronic focusing in the linear and sector scan according to said scanning control signal and scan select signal;

delay circuits controlled by the output of said delay time control circuit;

transducer means including at least one electronic linear scan probe having a plurality of ultrasonic transducers and at least one electronic sector scan probe having a plurality of ultrasonic transducers, said transducer means being driven by the output of said delay circuit to effect transmission of ultrasonic waves and reception of ultrasonic echoes on one of the linear and sector scan probes which is selected by said scanning control signal and scan select signal during said second period control pulse signal;

a transmission/reception circuit provided between said delay circuit and the transducer means and serving to supply drive signals to the ultrasonic transducers and receiving ultrasonic echo signals for processing thereof;

gate circuits for simultaneously supplying a drive signal to a predetermined number of said linear scan probe transducers at the time of said linear scan and for supplying a drive signal of a predetermined phase to said sector scan probe transducers at the time of said sector scan;

summing means for summing said received ultrasonic echoes;

signal processing means for processing said summed echo signals to produce a video signal suited for display;

display means for displaying images selectively obtained by the linear and sector scan probe through said signal processing means; and sweep signal generator means for producing X and Y sweep signals according to said scan select signal and reference control pulse signal and for supplying said X and Y sweep signals to said display means in accordance with the selected scan.

4. An ultrasonic diagnosing apparatus according to claim 3, wherein said scanning control circuit includes first address storing means for storing the addresses representing transducers in said linear scan probe and determining the addresses of said first address storing means during the first control pulse signal at the time of the linear scan and second address storing means for storing addresses representing sector scanning lines and determining the address of said first address storing means during the first control pulse signal at the time of said sector scan.

5. An ultrasonic diagnosing apparatus according to claim 3 or 4, wherein said delay time control circuit includes first delay time storing means for storing data representing delay times assigned to the transducers of said linear scan probe and for supplying each delay time of transducer addressed outputs of the first address storing means and second delay time storing means for storing data representing delay times assigned to the transducers of said sector scan probe and for supplying each delay time to the transducer corresponding to each sector scanning line.

6. An ultrasonic diagnosing apparatus comprising:

at least one ultrasonic linear scan probe including a plurality of ultrasonic transducers for effecting a linear scan of a subject under examination;

at least one ultrasonic sector scan probe including a plurality of ultrasonic transducers for effecting a sector scan of said subject;

scan mode control means for determining a scan mode combining said electronic linear scan and sector scan and producing a scan mode control signal;

scanning control means for alternately controlling the driving of the transducers of said linear and sector scan probes each for period corresponding to said scan mode control signal, respectively;

a delay circuit for controlling the timing of driving of the individual transducers in said electronic linear and sector scan probes;

a pulser for impressing drive pulses upon said individual transducers according to an input pulse signal coupled through said delay circuit to thereby cause emission of ultrasonic waves;

a summing circuit for summing up ultrasonic echo signals received by said transducers; and display means for displaying a tomogram according to the output signal of said summing circuit.

* * * * *